US012753160B2

(12) United States Patent
Lucarelli et al.

(10) Patent No.: US 12,753,160 B2
(45) Date of Patent: Oct. 6, 2026

(54) PROCESS FOR THE PREPARATION OF 3,4-METHYLENEDIOXYPROPIOPHENONE

(71) Applicant: Endura S.P.A., Bologna (IT)

(72) Inventors: Carlo Lucarelli, Bologna (IT); Tommaso Tabanelli, Cotignola (IT); Angelo Vaccari, Bologna (IT); Martina Eberle, Piovene Rocchette (IT); Carla Marchioro, Villafranca di Verona (IT); Matteo Campanati, Bologna (IT); Stefano Billi, Faenza (IT); Alberto Guerrini, Ravenna (IT); Nicola Schiaroli, Senigallia (IT)

(73) Assignee: Endura S.P.A., Bologna (IT)

( * ) Notice: Subject to any disclaimer, the term of this patent is extended or adjusted under 35 U.S.C. 154(b) by 523 days.

(21) Appl. No.: 18/274,089

(22) PCT Filed: Jan. 31, 2022

(86) PCT No.: PCT/EP2022/052218
§ 371 (c)(1),
(2) Date: Jul. 25, 2023

(87) PCT Pub. No.: WO2022/162223
PCT Pub. Date: Aug. 4, 2022

(65) Prior Publication Data

US 2024/0425471 A1 Dec. 26, 2024

(30) Foreign Application Priority Data

Jan. 29, 2021 (WO) ................. PCT/EP2021/052187

(51) Int. Cl.
*C07D 317/54* (2006.01)
*B01J 31/10* (2006.01)
*B01J 31/26* (2006.01)

(52) U.S. Cl.
CPC ............ *C07D 317/54* (2013.01); *B01J 31/10* (2013.01); *B01J 31/26* (2013.01)

(58) Field of Classification Search
None
See application file for complete search history.

(56) References Cited

U.S. PATENT DOCUMENTS 5,817,878 A * 10/1998 Spagnol ................... B01J 29/04 568/322
6,342,613 B1 * 1/2002 Borzatta ............. C07D 317/54 549/430

FOREIGN PATENT DOCUMENTS

WO WO 99/54041 * 10/1999
WO 0040575 A1 7/2000
WO 2020174271 A1 9/2020
WO WO 2020174271 * 9/2020

OTHER PUBLICATIONS

Koura et al. (Bioorganic & Medicinal Chemistry Letters 2015, 25(13), 2668-2674).*
Yadav (Organic Process Research and Development 2002, 6, 706-713).*
Sartori (Chem. Rev. 2011, 111, 5, PR181-PR214).*
Holderich (Applied Catalysis A: General 350 (2008) 1-5).*
Subramaniam (Journal of Catalysis 245 (2007) 184-190).*
Pande (Synthetic Communications (2011), 41:5, 754-761).*
https://webbook.nist.gov/cgi/cbook.cgi?Name=benzodioxole&Units=SI.*
Gelbard, G. , "Organic Synthesis by Catalysis with Ion-Exchange Resins", Ind. Eng. Chem. Res., 44(23), Oct. 14, 2005, 8468-8498.
Pande, M. A, et al., "Acylation of Aromatic Ethers Using Different Carboxylic Acid Anhydrides as Acylating Agents in the Presence of Nontoxic, Noncorrosive Resin Amberlyst 15 as a Solid Acid Catalyst", Synthetic Communications, 41 (5), Feb. 7, 2011, 754-761.
Sartori, G. , et al., "Use of Solid Catalysts in Friedel-Crafts Acylation Reactions +", Chem. Rev., 106(3), 2006, 1077-1104.
Wang, B-H. , et al., "ZnCl2-modified ion exchange resin as an efficient catalyst for the bisphenol-A production", Chinese Chem. Let., 25(11), Nov. 2014, 1423-1427.
Chaowu, X. , "Preparation of Sulfonated Ultrafine Polystyrene Resin", Synthetic Technology an Application, 23(4), 2008, 12-15; 23.

* cited by examiner

*Primary Examiner* — Valerie Rodriguez-Garcia
(74) *Attorney, Agent, or Firm* — Elmore Patent Law Group, P.C.; Joseph C. Zucchero; Carolyn S. Elmore

(57) ABSTRACT

The invention relates to a process for the preparation of 1-(1,3-benzodioxol-5-yl)-1-propanone comprising the step of reacting 3,4-methylendioxybenzene with propionic anhydride in the presence of a bulk or supported catalyst, being said catalyst selected from the group of a sulphonated cross-linked divinylbenzene resin, a sulphonated cross-linked divinylbenzene resin partially exchanged with iron, zinc or gallium, a perfluorinated sulphonic resin, and a perfluorinated sulphonic resin partially exchanged with iron, zinc or gallium, wherein said catalyst has an average particle size from 1 μm to 300 μm, preferably from 1 μm to 180 μm, more preferably from 1 μm to 100 μm as measured with DLS (Dynamic light scattering) or a granulometer. The process is advantageously carried out at stoichiometric ratio between the reagents and with a continuous process.

51 Claims, 2 Drawing Sheets

PROCESS FOR THE PREPARATION OF 3,4-METHYLENEDIOXYPROPIOPHENONE

FIELD OF THE INVENTION

The present invention relates to a new and inventive process for the preparation of 3,4-methylenedioxypropiophenone also known as 1-(1,3-benzodioxol-5-yl)-1-propanone as below represented.

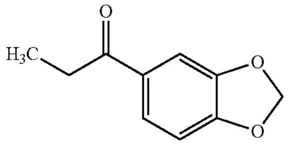

Such a process is an improved and commercially viable process working in solvent-free conditions and with a heterogeneous catalyst.

BACKGROUND

Alkylenedioxybenzene derivatives have gained much importance in the pharmaceutical, pesticide, biocide, performer, and food sectors due to their application as the final product or the intermediate of a desired final product.

For example, compounds having insecticidal activity containing the benzo[1,3]dioxole group have been described in numerous publications. Safrole and isosafrole are used in performary and specifically isosafrole is used for the synthesis of piperonal (benzo[1,3]dioxole-5-carboxyaldehyde) used for producing perfumes and aromas. Among aryl ketones, 3,4-Methylenedioxypropiophenone also known as 1-(1,3-benzodioxol-5-yl)-1-propanone is a crucial compound and an intermediate in the above fields.

In EP1140894B1 a method for the preparation of 5-(α-hydroxyalkyl)benzo[1,3]dioxoles is described, which provides for a step of preparation of the acyl derivative. Specifically the described process comprised a first step a) of preparing benzo[1,3]dioxole by reacting from 1,2-dihydroxybenzene and methylene chloride in a suitable solvent, followed by a step b) of reacting the so obianed benzo[1,3]dioxole with propionic anhydride in the presence of perchloric acid as acylation catalyst. In the description the proposed acylation catalysts were ZnO, $ZnCl_2$, $FeCl_2$, $FeCl_3$, $FeSO_4$, $Fe_2(SO_4)_3$, FeO, $Fe_2O_3$, $H_3PO_4$ and $HClO_4$.

Drawbacks associated to this kind of catalysts are reported in WO2020/174271. In this International application it is underlined that all these catalysts are toxic and corrosive and generally produce high amounts of hydrochloric acid in the effluent with a consequent huge amount of sludge, thus rendering the process highly polluting and environmentally harmful.

The same document thus proposes the use of an alkyl sulphonic acid to easily separate the unreacted carboxylic acid and unreacted substrate, that can be reused.

In example 14 of WO2020/174271, 3,4-methylenedioxypropiophenone is prepared by charging firstly methane sulphonic acid and propionic anhydride, and after cooling by adding 3,4-methylendioxybenzene. The reaction was maintained at 0° C. to 5° C. for 4 hours and after completion of the reaction, the reaction mass was diluted with water and the obtained 3,4-methylenedioxypropiophenone and the unreacted 3,4-methylenedioxybenzene were extracted with toluene. Distillation of the toluene layer allowed to recover unreacted 3,4-methylenedioxybenzene and to obtain 3,4-methylenedioxypropiophenone with a gas purity of 98%. They also recover in the aqueous phase 63 g of propionic acid The process therein described teaches the use of an excess of the homogenous catalyst, i.e. methane sulfonic acid, that needs to be recovered. In fact, the process provides for an extraction in water/toluene in order to recover not only the wished product (in toluene) but also the catalyst. The inventors studied the process and noted that the prior art process of WO2020/174271 was able to obtain higher 3,4-methylendioxybenzene conversion and yielded into the target product in view of the use of an excess of catalyst and very stringent condition of reaction (between 0 and 5° C. for four hours). Furthermore, it is well known that methyl sulphonic acid is corrosive for metals and difficult to manipulate even if used in industry.

It is also known that 3,4-methylendioxybenzene, being an aromatic cyclic ether, is characterized by a partial deactivation of the ring due to the bending of the group —CH2- in bridge position with respect to the two oxygen atoms (FT-IR Investigation of Methoxy Substituted Benzenes Adsorbed on Solid Acid Catalysts". J. Phys. Chem. C 2012, 116, 21308-21317. dx.doi.org/10.1021/jp3023056. "Anomeric Effect in 1,3-Dioxole: A Theoretical Study". J. Am. Chem. Soc. 1996, 118, 9850-9854.). Therefore stringent and drastic conditions for the acylation reaction as reported in WO2020/174271 are usually necessary.

Furthermore, as reported in WO 2018/150230, paragraph [0016], the acylation of alkylenedioxybenzene compounds using conventional processes results in synthesis of the end product in low yield and low purity, as —O—(CH2)m-O— ring of the reactant and product are very susceptible to cleavage under acid conditions.

Therefore, the object of the present invention is firstly to provide an economical, efficient, and environmentally friendly process for preparing 3,4-methylenedioxypropiophenone also known as 1-(1,3-benzodioxol-5-yl)-1-propanone, thus overcoming the drawbacks of the prior art process, and secondly acylating it with good yield and purity.

SUMMARY OF THE INVENTION

Notwithstanding the fact that the heterogeneous catalysts, specifically those based on sulphonated resins, are known for being very less active in catalyzing the acylation of substrates, even for open heterocycles as reported for example in "*Perfluorinated nafion-modified SBA*-15 *material for catalytic acylation of anisole*", Applied Catalyst A: General F. Martinez, G. Morales, A. Martin, R van Grieken, wherein many difficulties in acylating anisole are reported, the inventors found out that the heterogeneous catalysts in specific granule size are capable not only to increase the conversion from the starting material, i.e. 3,4-methylendioxybenzene, but also to increase its selectivity.

The inventors in fact found out that the specific size of the granules/particles of the specific sulphonated heterogeneous catalysts surprisingly increased the selectivity that usually decreases not only with the increase of the active surfaces of the particles/granules of the heterogeneous catalysts, but also with the increase of the aromatic substrate conversion due to the promotion of the consecutive reaction over the target product.

Therefore, the Applicant has surprisingly found out that an innovative family of heterogenous catalysts having specific particle sizes that could be efficiently used for the acylation of 3,4-methylendioxybenzene. These micronized catalysts not only were capable to increase the conversion, but also the selectivity of the acylation reaction on the substrate 3,4-methylendioxybenzene, that is a closed heterocycle. Therefore the invention relates to a process for the preparation of 1-(1,3-benzodioxol-5-yl)-1-propanone comprising the step of reacting with propionic anhydride in the presence of a bulk or supported catalyst, being said catalyst selected from the group consisting of a sulphonated cross-linked divinylbenzene resin, a sulphonated cross-linked divinylbenzene resin partially exchanged with iron, zinc or gallium, a perfluorinated sulphonic resin, and a perfluorinated sulphonic resin partially exchanged with iron, zinc or gallium, wherein said catalyst has an average particle size from 1 μm to 300 μm, preferably from 1 μm to 180 μm, more preferably from 1 μm to 100 μm as measured with DLS (Dynamic light scattering) or a granulometer.

When in the present invention the definition "particle size" is used is meant the average diameter of the single particle/granule of the final catalyst.

In an advantageous embodiment of the inventive process the catalyst has an average particle size from 40 μm to 100 μm.

In a preferred embodiment the catalyst is a supported catalyst on oxides, preferably supported on silica, zirconia, titania or alumina, more preferably silica.

The inventors hence surprisingly noted that the use of bulk or supported resins characterized by the presence of a sulfonic acid functional group showed peculiar catalytic activity in the acylation of 3,4-methylendioxybenzene with propionic anhydride. Furthermore, the inventors noted that the process of the acylation of 3,4-dimethylenedioxybenzene was extremely efficient when the catalyst was in form of powder, both used as bulk catalyst and as supported catalyst.

Advantageously, the catalyst of the process of the invention can be recovered, regenerated and recycled for starting again the reaction.

The herein used catalysts are suitable to being applied in both batch and continuous flow apparatus, leading to the selective formation of 3,4-methylenedioxypropiophenone.

In an advantageous embodiment, the process for preparing of 1-(1,3-benzodioxol-5-yl)-1-propanone is a continuous process.

From the above it is evident that the process of the invention is not only environmentally friendly with less severe conditions of operation with respect to the prior art process, but also extremely efficient for the production of 1-(1,3-benzodioxol-5-yl)-1-propanone with the possibility to work also in a continuous way.

DETAILED DESCRIPTION OF THE INVENTION

Figure 1:
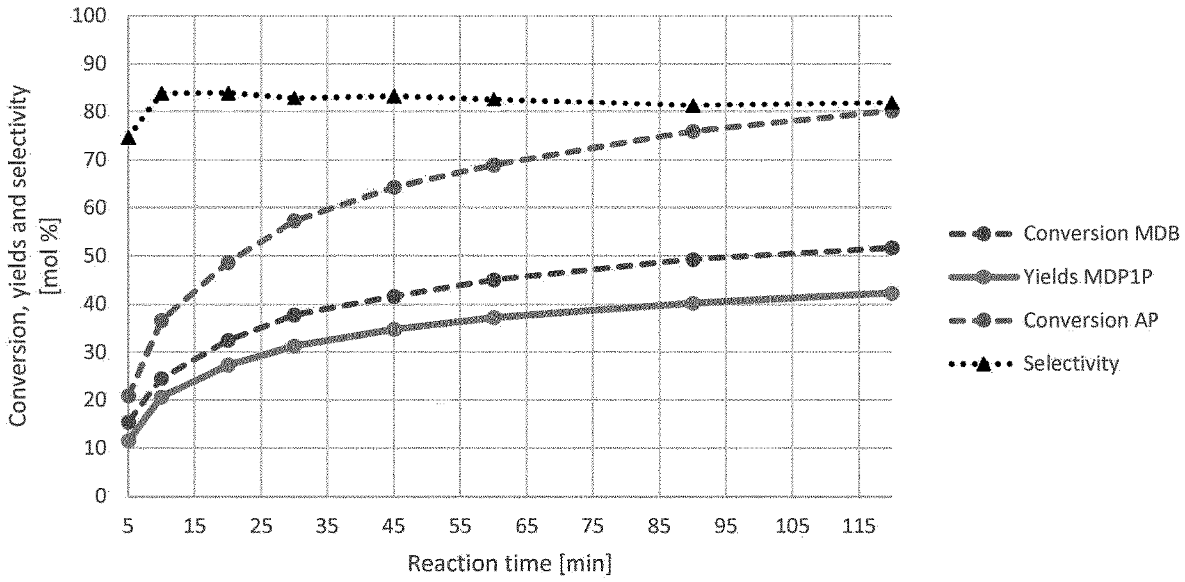
FIG. 1 represents the results of example 7.

The invention hence relates to a process for the preparation of 1-(1,3-benzodioxol-5-yl)-1-propanone comprising the step of reacting 3,4-methylendioxybenzene with propionic anhydride in the presence of a bulk or supported catalyst, being said catalyst selected from the group of a sulphonated cross-linked divinylbenzene resin, a sulphonated cross-linked divinylbenzene resin partially exchanged with iron, zinc or gallium, a perfluorinated sulphonic resin, and a perfluorinated sulphonic resin partially exchanged with iron, zinc or gallium, wherein said catalyst has an average particle size from 1 μm to 300 μm, preferably from 1 μm to 180 μm, more preferably from 1 μm to 100 μm as measured with DLS (Dynamic light scattering) or a granulometer.

When in the present invention the definition "particle size" is used is meant the average diameter of the single particle/granule of the final catalyst.

In an advantageous embodiment of the inventive process the catalyst has an average particle size from 40 μm to 100 μm.

The invention comprises the step of acylation reaction of 3,4-methylendioxybenzene in the presence of a bulk or supported catalyst selected from the group of a sulphonated cross-linked divinylbenzene resin, a sulphonated cross-linked divinylbenzene resin partially exchanged with iron, zinc or gallium, a perfluorinated sulphonic resin, and a perfluorinated sulphonic resin partially exchanged with iron, zinc or gallium, wherein said catalyst has an average particle size from 1 μm to 300 μm, preferably from 1 μm to 180 μm, more preferably from 1 μm to 100 μm as measured with DLS (Dynamic light scattering) or a granulometer.

All these catalysts are defined as heterogenous catalysts.

As it will be clearer from the experimental part the inventors tried to use the heterogeneous catalysts as available in the market directly in acylating 3,4-methylendioxybenzene, but the attempt leads to very poor results, specifically at low temperatures. The inventors found out that, when the catalyst has an average particle size from 1 μm to 300 μm, preferably from 1 μm to 180 μm, more preferably from 1 μm to 100 μm as measured with DLS (Dynamic light scattering) or a granulometer the acylation of MDB was possible with surprising results.

The catalyst can be a sulphonated cross-linked polystyrene-divinyl benzene resin used as bulk or supported on silica. Preferably, the sulphonated cross-linked polystyrene-divinyl benzene resin is characterized an acid loading expressed as mmol of group —$SO_3H$ per g of material in the range from 2 to 6, more preferably 2.5 to 5.5, still more preferably about 5.

The catalyst can be a perfluorinated sulphonic acid resins used as bulk or supported on silica. Preferably the perfluorinated sulphonic acid resin is characterized by an acid loading expressed as mmol of group —$SO_3H$ per g of material in the range from 0.2 to 2, more preferably from 0.7 to 1.6, still more preferably the catalyst has an acid loading of about 1.2.

In a preferred embodiment the catalysts above indicated are commercially available catalysts that are subjected to a micronization step in order to have particle size in the range from 1 μm to 300 μm, preferably from 1 μm to 180 μm, more preferably from 1 μm to 100 μm as measured with DLS (Dynamic light scattering) or a granulometer. The sulphonated cross-linked polystyrene-divinyl benzene resin can be the product AMBERLYST®, an exchange ion resin available from Rohm and Haas Company. These resins can be the product named as:

AMBERLYST® 15 having an acid loading (expressed as mmol of group —$SO_3H$ per g of material) of 4.7 (https://www.sigmaaldrich.com/catalog/product/aldrich/216399), AMBERLYST® 36 having an acid loading (expressed as mmol of group —$SO_3H$ per g of material) of 5.4 (Sibao Liu and others, 'Renewable Lubricants with Tailored Molecular Architecture', Science Advances, 5.2 (2019) (https://doi.org/10.1126/sciadv. aav5487)), AMBERLYST® 39 having an acid loading (expressed as mmol of group —$SO_3H$ per g of material) of 5 (Tomasz Komon and others, 'Esterification of Acrylic Acid with 2-Ethylhexan-1-Ol: Thermodynamic and Kinetic Study', Applied Catalysis A: General, 451 (2013), 127-36 (https://doi.org/10.1016/j.apcata.2012.11.018)) or AMBERLYST® 70 having an acid loading (expressed as mmol of group —$SO_3H$ per g of material) of 2.55 (Tomasz Komon and others, 'Esterification of Acrylic Acid with 2-Ethylhexan-1-Ol: Thermodynamic and Kinetic Study', Applied Catalysis A: General, 451 (2013), 127-36 (https://doi.org/10.1016/j.apcata.2012.11.018)).

The perfluorinated sulphonic acid resin can be the product AQUIVION®, a perfluorinated resin having the following structure

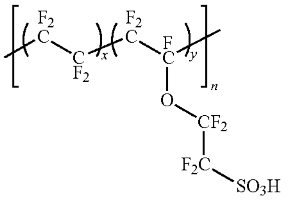

The presence of the terminal —$CF_2CF_2SO_3H$ groups renders the perfluorinated resin strongly acidic.

The resin AQUIVION® can be a commercial product named as AQUIVION® PW79S that is a coarse, acid perfluorinated resin powder based on the short-side-chain (SSC) copolymer of Tetrafluoroethylene and the Sulfonyl Fluoride Vinyl Ether (SFVE) $CF_2$═CF—O—$(CF_2)_2$—$SO_2F$ produced by Solvay and having an acid loading of 1.27.

The resin AQUIVION® can be a commercial product named as AQUIVION® P98-S, that is perfluorinated pellets in the sulfonyl fluoride (—$SO_2F$) form that exhibit an Equivalent Weight (EW) of 980 g/eq. This perfluorinated resin is based on the unique Short Side Chain copolymer of Tetrafluoroethylene (TFE) and Sulfonyl Fluoride Vinyl Ether (SFVE) $CF_2$═CF—O—$(CF_2)_2$—$SO_2F$ produced by Solvay and having an acid loading expressed as mmol of group —$SO_3H$ per g of material of 1.02.

The resin AQUIVION® can be a commercial product named as AQUIVION® PW87-S, that is perfluorinated resin in form of powder. This perfluorinated resin is based on the unique Short Side Chain copolymer of Tetrafluoroethylene (TFE) and Sulfonyl Fluoride Vinyl Ether (SFVE) $CF_2$═CF—O—$(CF_2)_2$—$SO_2F$ produced by Solvay and having an acid loading expressed as mmol of group —$SO_3H$ per g of material of 1.15.

The use of other resins AQUIVION® available in the market or as in the present experimental part is contemplated according to the present invention.

The perfluorinated sulphonic acid resin can be the product NAFION™, a perfluorinated resin having the following structure

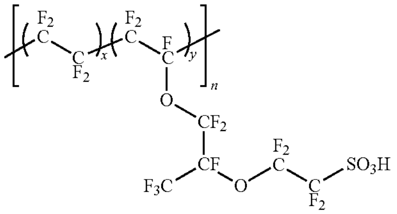

NAFION's™ unique ionic properties are a result of incorporating perfluorovinyl ether groups terminated with sulfonate groups onto a tetrafluoroethylene (PTFE) backbone. The resin NAFION™ can be a commercial product named as NAFION™ NR50 that is a perfluorosulfonic acid nafion resin with high thermal stability and chemical resistance in the form of pellets. This perfluorinated resin is produced by DuPont and having an acid loading expressed as mmol of group —$SO_3H$ per g of material of 0.8.

The use of other resins NAFION™ available in the market or as in the present experimental part is contemplated according to the present invention.

The heterogeneous catalysts of the invention are hence characterized by the presence of sulphonic acid groups and can be also partially or completely exchanged with iron or zinc or gallium.

In fact, the catalytic material herein reported (acid resins) can be modified by exchange of the acidic proton with a metal ion selected from iron (Fe), zinc (Zn) and gallium (Ga). The procedure to be used for exchanging the hydrogen ion on a sulphonated cross-linked polystyrene-divinyl benzene resin or a perfluorinated sulphonic acid resin is reported in literature, for example in Journal of Molecular Catalysis A: Chemical 411 (2016) 257-263).

Surprisingly, the modification of the catalyst in terms of acid sites density, strength, and accessibility due to the presence of the metal ion Fe, Zn or Ga strongly affects the reactivity of the MDB in terms of conversion and selectivity towards the product.

When in the present invention the sulphoned resin catalyst is exchanged it is partially exchanged.

According to the invention a partial exchange means a percentage of hydrogen atom from 5 to 80% with a metal ion selected from Fe, Zn and Ga. Preferably the exchange percentage is from 10 to 50%, more preferably it is about 30%.

Examples of resins partially exchanged with Fe can be prepared by following the above literature and using AQUIVION® PW87-S in form of powders.

The final exchanged sulphonated catalysts is hence subjected to a micronization step thus having a particle size in the range from 1 μm to 300 μm, preferably from 1 μm to 180 μm, more preferably from 1 μm to 100 μm as measured with DLS (Dynamic light scattering) or a granulometer. The mentioned materials can be used as catalyst in the process of the invention supplied or supported over suitable inorganic oxides.

A suitable inorganic oxide can be silica, zirconia, titania and alumina, preferably it is silica. In particular, the supported materials may be commercially available products or be prepared as described in the literature, for example as described in the Italian patent 102018000006967.

The catalyst can be hence supported according to general procedure known in the art. A preferred procedure for preparing supported catalysts according to the invention is reported in the experimental part by way of example.

The above-mentioned resins named as AMBERLYST® AQUIVION® and NAFION™ can be supported over suitable inorganic oxides. For example, AQUIVION® D79 can be supported on zirconia or on silica, while AQUIVION® PW98-S can be supported on alumina. NAFION™ supported on silica is also available on the market by Dupont or Merk.

The resins used as catalysts in the present invention can be supported on the inorganic oxides, preferably silica, alumina, titania, and zirconia in a percentage by weight (%) from 1 to 60, more preferably 5-30%, still more preferably from 10 to 15% by weight with respect to the total weight of the supported catalyst.

The final supported sulphonated catalysts during the synthesis steps is shaped so as to obtain a particle size ranging from 1 μm to 300 μm, preferably from 1 μm to 180 μm, more preferably from 1 μm to 100 μm as measured with DLS (Dynamic light scattering) or a granulometer.

In a preferred embodiment the catalyst used in the invention can be:

a sulphonated cross-linked divinylbenzene resin partially exchanged with iron, zinc or gallium and supported on an inorganic oxide, or a perfluorinated sulphonic resin partially exchanged with iron, zinc or gallium and supported on an inorganic oxide.

The final supported exchanged sulphonated catalysts during the synthesis steps is shaped so as to obtain a particle size ranging 1 μm to 300 μm, preferably from 1 μm to 180 μm, more preferably from 1 μm to 100 μm as measured with DLS (Dynamic light scattering) or a granulometer.

In one embodiment of the process of the invention the step of reacting 3,4-methylendioxybenzene with propionic anhydride in the presence of a bulk or supported catalyst, previously subjected to a micronization step or produced in a precise range of particle size according to the invention (a particle size ranging from 1 μm to 300 μm, preferably from 1 μm to 180 μm, more preferably from 1 μm to 100 μm as measured with DLS (Dynamic light scattering) or a granulometer), selected from the group of a perfluorinated sulphonic resin, and a perfluorinated sulphonic resin partially exchanged with iron, zinc or gallium is carried out in the range of temperature from 50 to 200° C., more preferably 60 to 150° C., still more preferably about 80° C. In this embodiment of the invention the reaction time is from 5 to 240 min, more preferably from 5 to 120 min, still more preferably about 60 min.

In another embodiment of the process of the invention the step of reacting 3,4-methylendioxybenzene with propionic anhydride in the presence of a bulk or supported catalyst, previously subjected to a micronization step or produced in a precise range of particle size according to the invention (a particle size ranging from 1 μm to 300 μm, preferably from 1 μm to 180 μm, more preferably from 1 μm to 100 μm as measured with DLS (Dynamic light scattering) or a granulometer), selected from the group of a sulphonated cross-linked divinylbenzene resin, a sulphonated cross-linked divinylbenzene resin partially exchanged with iron, zinc or gallium is carried out in the range of temperature from 50 to 150° C., more preferably 60 to 130° C., still more preferably about 80° C. or 120° C. In this embodiment of the invention the reaction time is from 5 to 240 min, more preferably from 5 to 120 min, still more preferably about 60 min.

In a preferred embodiment the process is performed in a batch reactor, more preferably under solvent free condition, loading a genuine catalytic amount of the catalyst.

The amount of catalyst is expressed as ratio between mol of H+ or of active sites per mol of limiting reagent, generally 3,4-dimethelendioxybenzene.

In case of a bulk or supported catalyst selected from the group of a perfluorinated sulphonic resin, and a perfluorinated sulphonic resin partially exchanged with iron, zinc or gallium the ratio is preferably from 0.0001 to 1, more preferably from 0.001 to 0.04 still more preferably about 0.007.

In case of a bulk or supported catalyst selected from the group of a sulphonated cross-linked divinylbenzene resin, a sulphonated cross-linked divinylbenzene resin partially exchanged with iron, zinc or gallium the ratio is from 0.002 to 1, more preferably from 0.01 to 0.08, still more preferably about 0.03.

Advantageously the step of reacting 3,4-methylendioxybenzene with propionic anhydride is carried out preferably with a molar ratio between 3,4-methylendioxybenzene and propionic anhydride in the range from 2 to 1 to 1 to 2, more preferably in 1:1 stoichiometric ratio.

The stoichiometric ratio is more preferred, therefore with no need of a consistent excess of one of the two reagents.

In an advantageous aspect, the catalyst of the present process can be recovered, regenerated, and recycled.

In a preferred embodiment the catalyst can be recovered by filtration from the reaction medium and suspension in a diluted acid aqueous solution of nitric acid, preferably at a concentration in the range from 2% wt to 60% wt, more preferably from 10 to 40%, still more preferably of 20% wt.

In another preferred embodiment the catalyst can be recovered by filtration from the reaction medium and suspension in a diluted acid aqueous solution of hydrochloric acid, preferably at a concentration in the range from 2% wt to 30% wt, more preferably 20% wt.

The recovery of the catalyst is preferably carried out at a temperature in the range from room temperature to reflux for a time in the range from few minutes to 4 hours, more preferably 1 hour.

The recovery of the catalyst is hence a regeneration treatment. After the regeneration treatment, the catalyst can be recovered by filtration, washed with water until a neutral pH of the mother solution is achieved and dried at about 120° C. for about one hour. The so obtained material, i.e. the catalyst of the invention, can be recycled for another reaction.

Furthermore, the herein reported catalytic materials are suitable to being applied in both batch and continuous flow apparatus, leading to the selective formation of 3,4-methylenedioxypropiophenone.

The inventors hence surprisingly noted that the use of bulk or supported resins having granules/particles in specific size range and characterized by the presence of sulphonic acid functional groups show peculiar catalytic activity in the acylation of 3,4-methylendioxybenzene with propionic anhydride. Furthermore, the inventors noted that the process of the acylation of 3,4-dimethylenedioxybenzene was extremely efficient even on a very little reactive starting material as 3,4-dimethylenedioxybenzene when the catalyst was in form of a powder, both used as bulk catalyst and as supported catalyst, having a particle size range from 1 μm to 300 μm, preferably from 1 μm to 180 μm, more preferably from 1 μm to 100 μm as measured with DLS (Dynamic light scattering) or a granulometer.

Advantageously, the catalyst of the process of the invention can be recovered, regenerated and recycled for starting again the reaction.

In an advantageous embodiment, the process for preparing of 1-(1,3-benzodioxol-5-yl)-1-propanone is a continuous process.

From the above it is evident that the process of the invention is not only environmentally friendly with less severe conditions of operation with respect to the prior art process, solvent free conditions, but also extremely efficient for the production of 1-(1,3 -benzodioxol-5-yl)-1-propanone with the possibility to work also in a continuous way. Surprisingly, the process of the invention has no need of a consistent excess of one of the two reagents and showed short reaction time and relatively low reaction temperature. The process is further characterized by an easy recovery, regeneration and recycle of the catalyst.

Without being bound to any theory the inventors deem that it is of fundamental importance to cover the possibility to support the present heterogeneous catalyst over suitable supports, having with high pore volume and/or high surface area.

Features and advantages of the invention will also appear more clearly from the following non-limiting examples.

EXPERIMENTAL PART

The following acronyms were used for indicating ingredients/products/effect in the experimental part:

| | |
|---|---|
| MBD = | 3,4-methylenedioxybenzene |
| AP = | propionic anhydride |
| MDP1P = | 3,4-methylenedioxypropriophenone |
| X = | conversion |
| Y = | yield |
| S = | selectivity |

Example 1

Acylation of MDB with AQUIVION® PW87 as Available on the Market 2.126 grams of 3,4-methylenedioxybenzene (MBD) and 2.2924 grams of propionic anhydride were loaded inside a 25 mL two-necked round bottom flask and stirred to get a homogeneous solution. After that 0.0988 grams of catalyst (AQUIVION® PW87-S, corresponding to a mol ratio between active acid sites and MDB equal to 0.007), as available on the market having a particle size ranging from 0.6 mm to 1.1 mm as measured with DLS (Dynamic light scattering) or a granulometer, was inserted inside the liquid mixture and the flask was equipped with two condensers. The reaction mixture was then inserted in a pre-heated oil bath at 80° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 ml of acetone HPLC grade, 20 µL of octane was used as internal standard for the gas-chromatograph quantifications. The analysis of the products at the end of the reaction was carried out by a GC equipped with an HP-5 (Agilent) capillary column (the temperature ramp used consisted of 6 minutes at 35° C. followed by heating with a speed of 10.00° C./min up to 280° C.), and a flame ionization detector (FID). The results were the following: MDB conversion of 40%, propionic anhydride conversion of 64%, 3,4-methylenedioxypropiophenone yield of 26% and selectivity of 64%.

Example 2

Preparation of 3,4-Methylenedioxypropiophenone with Catalyst AQUIVION® PW87-S at 80° C., 1 h According to the Invention 2.126 grams of 3,4-methylenedioxybenzene (MBD) and 2.2924 grams of propionic anhydride were loaded inside a 25 mL two-necked round bottom flask and stirred to get a homogeneous solution. After that 0.0988 grams of catalyst (AQUIVION® PW87-S, corresponding to a mol ratio between active acid sites and MDB equal to 0.007), previously subjected to a micronization process to a particle size ranging from 40 µm to 100 µm as measured with DLS (Dynamic light scattering) or a granulometer, was inserted inside the liquid mixture and the flask was equipped with two condensers. The reaction mixture was then inserted in a pre-heated oil bath at 80° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 µL of octane was used as internal standard for the gas-chromatograph quantifications. The analysis of the products at the end of the reaction was carried out by a GC equipped with an HP-5 (Agilent) capillary column (the temperature ramp used consisted of 6 minutes at 35° C. followed by heating with a speed of 10.00° C./min up to 280° C.), and a flame ionization detector (FID). The results were the following: MDB conversion of 50%, propionic anhydride conversion of 77%, 3,4-methylenedioxypropiophenone yield of 41% and selectivity of 82%. The inventors hence noted that the catalyst when in the specific inventive granule/particle size allowed not only a higher conversion of the initial products but also a higher selectivity, that was not expected by reducing the particle size of the catalyst.

Example 3

Influence of the Particle Size on the Catalytic Activity of AQUIVION® PW87

The influence of the catalyst particle size on the catalytic activity on the acylation of MDB was investigated as described in example 2 by changing only the particle size of the catalyst. The results are reported in the following table X.

| µm | X MDB (%) | X AP (%) | S MDP1P (%) | Y ACP (%) | Y MDP1P (%) | Y By-products |
|---|---|---|---|---|---|---|
| 841-595 | 40 | 64 | 64 | 100 | 26 | 14 |
| 595-400 | 40 | 65 | 70 | 100 | 28 | 12 |
| 400-250 | 45 | 73 | 72 | 100 | 32 | 13 |
| 250-177 | 48 | 75 | 73 | 100 | 35 | 13 |
| 177-100 | 50 | 81 | 75 | 100 | 37 | 13 |
| 100-40 | 50 | 77 | 82 | 100 | 41 | 9 |
| 40-1 | 51 | 78 | 82 | 100 | 42 | 9 |

The catalyst particle size plays a fundamental role in the reaction. The decrease of the particle size led to an improvement of the MDB conversion that mainly depends on the catalyst active surface (which increases as the particle diameters become smaller). Surprisingly, also the reaction selectivity towards MDP1P was highly improved when the catalyst particle size was decreased.

Example 4

Evaluation of the Temperature Effect in the Presence of Catalyst AQUIVION® PW87-S Other four reactions were performed as described in example 2 by changing only the reaction temperature namely: 60° C., 80° C., 100° C. and 120° C. The results are reported in Table 1.

TABLE 1

| T (° C.) | X MDB (%) | X AP (%) | Y MDP1P (%) | Y ACP (%) | S MDP1P (%) | By-products (%) |
|---|---|---|---|---|---|---|
| 120 | 74 | 100 | 51 | 100 | 69 | 22 |
| 100 | 62 | 92 | 48 | 100 | 77 | 14 |
| 80 | 49 | 80 | 40 | 99 | 82 | 8 |
| 60 | 37 | 72 | 31 | 99 | 84 | 5 |

As in example 2, reaction conditions were the following: mol ratio between active acid sites and MDB equal to 0.007; MDB:AP=1:1; reaction time 1 h.

It was noted that the increase of the reaction temperature led to an increase in the conversion of both reagents (as expected from the foster of the kinetics) however the increase of the MDP1P yield is not linear therefore a slight decline in the selectivity was observed, favoring the formation of by-products (polyalkylated and others).

At any rate, all the temperatures resulted to be efficient in having high yield balanced with the achieved selectivity.

Example 5

Scale-Up Tests to 40 ml 20.21 grams of MDB and 21.74 grams of propionic anhydride were loaded inside a 250 mL three-necked round bottom flask and stirred to get a homogeneous solution. The reagent mix was heated in an oil bath at 80° C. and after that 0.9363 grams of catalyst AQUIVION® PW87-S, corresponding to a mol ratio between active acid sites and MDB equal to 0.007) previously subjected to a micronization process to a particle size ranging from 40 μm to 100 μm as measured with DLS (Dynamic light scattering) or a granulometer, was inserted inside the flask which was equipped with two condensers and a thermometer. The reaction was performed under magnetic stirring (720 rpm) for 1 hour. After the reaction, the mixture was rapidly cooled in an ice bath and the reaction mixture is recovered in 500 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with an HP-5 (Agilent) capillary column, and a flame ionization detector (FID). The results were the following: MDB conversion of 53%, propionic anhydride conversion of 82%, 3,4-methylenedioxypropiophenone yield of 43% and selectivity of 81%.

It was shown that the increase of a x10 factor (in comparison with example 1) did not affect the conversion nor the yield.

Example 6

Scale-Up to 400 mL 202.16 grams of MDB and 217.22 grams of propionic anhydride were loaded inside a 1 L jacketed reactor equipped with a mechanical stirrer, reflux condenser and a thermometer. The reagent mix was heated until 80° C. and after that 9.3586 grams of catalyst AQUIVION® PW87-S, corresponding to a mol ratio between active acid sites and MDB equal to 0.007) previously subjected to a micronization process to a particle size ranging from 40 μm to 100 μm as measured with DLS (Dynamic light scattering) or a granulometer, was inserted inside. The reaction was performed under mechanical stirring (250 rpm) for 1 hour. After the reaction, 2 mL of the reaction mixture was sampled and separated from the catalyst by filtration. 50 μL of the mixture was diluted in 10 mL of acetone HPLC grade, 20 μL of octane was used as internal standard for the gas-chromatograph quantifications. The analysis of the products at the end of the reaction was carried out by a GC equipped with an HP-5 (Agilent) capillary column, and a flame ionization detector (FID). The results were the following: MDB conversion of 46%, propionic anhydride conversion of 71%, 3,4-methylenedioxypropiophenone yield of 38% and selectivity of 82%.

Example 7

Evaluation of the Reaction Time Effect for PW87-S in a Reaction as Described in Example 6

The reaction was repeated as described in example 5 with the aim of investigate the effect of reaction time on a bigger scale reactor. To do so the reaction mixture was sampled at different time as reported in example 5. The results are reported in Table 2 below and represented in FIG. 1.

TABLE 2

| Time (min) | X MDB (%) | X AP (%) | Y MDP1P (%) | Y ACP (%) | S MDP1P (%) | Y By-products (%) |
|---|---|---|---|---|---|---|
| 5 | 15 | 21 | 11 | 23 | 75 | 4 |
| 10 | 25 | 37 | 21 | 42 | 84 | 5 |
| 20 | 32 | 49 | 27 | 53 | 84 | 6 |
| 30 | 38 | 57 | 31 | 65 | 83 | 7 |
| 45 | 42 | 64 | 35 | 74 | 83 | 8 |
| 60 | 45 | 69 | 37 | 73 | 83 | 8 |
| 90 | 49 | 76 | 40 | 85 | 81 | 9 |
| 120 | 52 | 80 | 42 | 90 | 82 | 11 |

By sampling the reaction mixture at different time it was possible to verify that during the reaction the selectivity to the desired product did not change. The conversion increased with reaction time as the yield in the desire product. The best compromise between yield and reaction time was 1 h but, it was possible to obtain about the same results stopping the reaction after 30 min. In the latter case the conversion of MDB and yield in the product were few point % lower but it was possible to double the number of catalytic cycles per day increasing the overall yield. Increasing the reaction time till 2 h it was possible to increases conversion and yield without a decrease of selectivity in order to reduce the amount of reactant that had to be recycled.

Example 8

Evaluation of Preferred Conditions when AQUIVION® PW79 is the Catalyst 2.1305 grams of MDB and 2.2879 grams of propionic anhydride were loaded inside a 25 mL two-necked round bottom flask and stirred to get a homogeneous solution. After that 0.0900 grams of catalyst AQUIVION® PW79, corresponding to a molar ratio between active acid sites and MDB equal to 0.007) previously subjected to a micronization process to a particle size ranging from 40 µm to 100 µm as measured with DLS (Dynamic light scattering) or a granulometer, was inserted inside the liquid mixture and the flask was equipped with two condensers. The reaction mixture was then inserted in a pre-heated oil bath at 120° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 µL of octane was used as internal standard for the gas-chromatograph quantifications. The analysis of the products at the end of the reaction was carried out by a GC equipped with an HP-5 (Agilent) capillary column, and a flame ionization detector (FID). The results were the following: MDB conversion of 64%, propionic anhydride conversion of 92%, 3,4-methylenedioxypropiophenone yield of 47% and selectivity of 73%.

Example 9

Acylation of MDB with Catalyst AQUIVION® PW98 as Available on the Market 2.1307 grams of MDB and 2.2879 grams of propionic anhydride were loaded inside a 25 mL two-necked round bottom flask and stirred to get a homogeneous solution. After that 0.1117 grams of catalyst AQUIVION® PW98, corresponding to a mol ratio between active acid sites and MDB equal to 0.007) as available on the market having a particle size ranging from 1.4 mm to 2.4 mm as measured with a granulometer, was inserted inside the liquid mixture and the flask was equipped with two condensers. The reaction mixture was then inserted in a pre-heated oil bath at 100° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 ml of acetone HPLC grade, 20 µL of octane was used as internal standard for the gas-chromatograph quantifications. The analysis of the products at the end of the reaction was carried out by a GC equipped with an HP-5 (Agilent) capillary column, and a flame ionization detector (FID). The results were the following: MDB conversion of 11%, propionic anhydride conversion of 18%, 3,4-methylenedioxypropiophenone yield of 7% and selectivity of 55%.

Example 10

Acylation of MDB with Catalyst AQUIVION® PW98 According to the Invention 2.1307 grams of MDB and 2.2879 grams of propionic anhydride were loaded inside a 25 mL two-necked round bottom flask and stirred to get a homogeneous solution. After that 0.1117 grams of catalyst AQUIVION® PW98, corresponding to a mol ratio between active acid sites and MDB equal to 0.007) previously subjected to a micronization process to a particle size ranging from 40 µm to 100 µm as measured with DLS (Dynamic light scattering) or a granulometer, was inserted inside the liquid mixture and the flask was equipped with two condensers. The reaction mixture was then inserted in a pre-heated oil bath at 100° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 µL of octane was used as internal standard for the gas-chromatograph quantifications. The analysis of the products at the end of the reaction was carried out by a GC equipped with an HP-5 (Agilent) capillary column, and a flame ionization detector (FID). The results were the following: MDB conversion of 40%, propionic anhydride conversion of 64%, 3,4-methylenedioxypropiophenone yield of 29% and selectivity of 72%.

Example 11

Process of the Invention with Catalyst AQUIVION® D79 Supported Over Silica 2.1282 grams of MDB and 2.2860 grams of propionic anhydride were loaded inside a 25 mL two-necked round bottom flask and stirred to get a homogeneous solution. After that 0.2999 grams of catalyst AQUIVION® D79 30% over silica, corresponding to a mol ratio between active acid sites and MDB equal to 0.007) characterized by a particle size ranging from 40 µm to 100 µm as measured with DLS (Dynamic light scattering) or a granulometer, was inserted inside the liquid mixture and the flask was equipped with two condensers. The reaction mixture was then inserted in a pre-heated oil bath at 120° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 µL of octane was used as internal standard for the gas-chromatograph quantifications. The analysis of the products at the end of the reaction was carried out by a GC equipped with an HP-5 (Agilent) capillary column, and a flame ionization detector (FID). The results were the following: MDB conversion of 65%, propionic anhydride conversion of 95%, 3,4-methylenedioxypropiophenone yield of 47% and selectivity of 72%.

Example 12

Lab Scale Regeneration General Procedure of the Catalyst in the Invention Process Firstly, the catalyst was separated from the reaction solution by filtrating on a Büchner funnel fitted with a filtering aid. Considering 0.1 g of exhaust catalyst, this was washed with acetone HPLC (25 mL) in order to remove all the weakly adsorbed reactants and products remained after reaction and finely pulverized in a mortar. After that the catalyst was inserted inside the flask equipped with two condensers. 5 mL of 20 wt % of $HNO_3$ (or HCl) solution were then used to regenerate the catalyst under reflux for 1 h. The resultant suspension was then cooled down and separated from the solution by filtration on a Buchner funnel fitted with a filtering aid. The catalyst was washed with water until neutral pH and afterwards washed again with acetone HPLC. Before the catalytic test, the catalyst was dried into an oven at 120° C. for 1 h.

Example 13

Recycle Test with Catalyst Pw87-S, Regeneration with Nitric Acid

The catalyst from Example 5 was regenerated as in Example 12 with 50 mL of solution of $HNO_3$ 20% w/w at 100° C. for 1 h.

13.61 grams of MDB and 14.57 grams of propionic anhydride were loaded inside a 250 mL three-necked round bottom flask and stirred to get a homogeneous solution. The reagent mix was heated in an oil bath at 80° C. and after that 0.6299 grams of regenerated catalyst AQUIVION® PW87-S, corresponding to a mol ratio between active acid sites and MDB equal to 0.007), previously subjected to a micronization process to a particle size ranging from 40 μm to 100 μm as measured with DLS (Dynamic light scattering) or a granulometer, was inserted inside the flask which was equipped with two condensers and a thermometer. The reaction was performed under magnetic stirring (720 rpm) for 1 hour. After the reaction, 2 mL of the reaction mixture was sampled and separated from the catalyst by filtration. 50 μL of the mixture is dilute in 10 mL of acetone HPLC grade, 20 μL of octane was used as internal standard for the gas-chromatograph quantifications. The analysis of the products at the end of the reaction was carried out by a GC equipped with an HP-5 (Agilent) capillary column (the temperature ramp used consisted of 6 minutes at 35° C. followed by heating with a speed of 10.00° C./min up to 280° C.), and a flame ionization detector (FID).

Catalyst recovery and regeneration as described in Example 12 were done for five times in order to test the recyclability of the material in few catalytic runs. The results are reported in the following table 3.

TABLE 3

| Cycle | X MDB (%) | X AP (%) | Y MDP1P (%) | Y ACP (%) | S MDP1P (%) | Y By-products (%) |
|---|---|---|---|---|---|---|
| | 53 | 82 | 43 | 100 | 81 | 9 |
| 1 | 50 | 73 | 38 | 77 | 76 | 11 |
| 2 | 49 | 75 | 39 | 81 | 79 | 10 |
| 3 | 46 | 71 | 37 | 80 | 80 | 9 |
| 4 | 51 | 75 | 40 | 76 | 78 | 10 |
| 5 | 50 | 79 | 38 | 99 | 76 | 11 |

Reaction conditions: mol ratio between active acid sites and MDB equal to 0.007; MDB:AP=1:1; reaction temperature 80° C.; reaction time 1 h.

The catalyst was recovered and recycled several times by using nitric acid with evident advantages in terms of process efficiency.

Example 14

Recycle Test with Catalyst AQUIVION® PW87-S, Regeneration with Hydrochloric Acid 2.1284 grams of MDB and 2.2935 grams of propionic anhydride were loaded inside a 25 mL two-necked round bottom flask and stirred to get a homogeneous solution. After that 0.0990 grams of catalyst AQUIVION® PW87-S, corresponding to a mol ratio between active acid sites and MDB equal to 0.007) previously subjected to a micronization process to a particle size ranging from 40 μm to 100 μm as measured with DLS (Dynamic light scattering) or a granulometer, was inserted inside the liquid mixture and the flask was equipped with two condensers. The reaction mixture was then inserted in a pre-heated oil bath at 120° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with an HP-5 (Agilent) capillary column (the temperature ramp used consisted of 6 minutes at 35° C. followed by heating with a speed of 10.00° C./min up to 280° C.), and a flame ionization detector (FID). After that, the catalyst was regenerated as in Example 12 with 5 mL of solution of HCl 20% w/w at 100° C. for 1 h, recovered, washed and dried as previously reported and tested in the same conditions for the acylation reaction. The results were reported in the following table 4.

TABLE 4

| Cycle | X MDB (%) | X AP (%) | Y MDP1P (%) | Y ACP (%) | S MDP1P (%) | Y By-products (%) |
|---|---|---|---|---|---|---|
| | 73 | 100 | 44 | 100 | 60 | 28 |
| 1 | 68 | 98 | 42 | 100 | 62 | 26 |

Reaction conditions: molar ratio between active acid sites and MDB equal to 0.007; MDB:AP=1:1; reaction temperature 120° C.; reaction time 1 h.

The catalyst was recovered and recycled by using hydrochloric acid with evident advantages in terms of process efficiency.

Example 15

Effect of the Molar Ratios Between the Reagents Over the Catalyst AQUIVION® PW87-S as Micronized According to the Invention Other four reactions were performed as described in example 2 by changing only the molar ratio between reagents, mol MDB/mol AP ranging from 1:1, 1.4:1, 2:1 and 1:2. The results were reported in the following Table 5.

TABLE 5

| Catalyst (gr) | MDB (gr) | AP (gr) | MDB: AP | X MDB (%) | X AP (%) | Y MDP1P (%) | Y ACP (%) | S MDP1P (%) | Y By-products (%) |
|---|---|---|---|---|---|---|---|---|---|
| 0.0989 | 2.1270 | 4.5595 | 1:2 | 60 | 69 | 39 | 87 | 65 | 20 |
| 0.0990 | 2.1311 | 2.2873 | 1:1 | 49 | 80 | 40 | 99 | 81 | 10 |

TABLE 5-continued

| Catalyst (gr) | MDB (gr) | AP (gr) | MDB: AP | X MDB (%) | X AP (%) | Y MDP1P (%) | Y ACP (%) | S MDP1P (%) | Y By-products (%) |
|---|---|---|---|---|---|---|---|---|---|
| 0.0986 | 2.9792 | 2.2992 | 1.4:1 | 36 | 69 | 30 | 73 | 83 | 6 |
| 0.0990 | 4.2561 | 2.2801 | 2:1 | 16 | 45 | 13 | 49 | 81 | 3 |

Reaction conditions: molar ratio between active acid sites and limiting reagent equal to 0.007; temperature 80° C.; reaction time 1 h.

The increase of the excess of AP led to a higher conversion value for 3,4-methylendioxybenzene but with a detrimental effect on the selectivity, on the other hand working with a slight excess of MDB led to a more selective conversion of AP toward the target product. In any case, the best compromise between MDB conversion and selectivity toward the MDP1P product was the stoichiometric amount of the reagents.

Example 16

Effect of the Catalyst Loading with AQUIVION® PW87-S as Function of Molar Ratio Between Active Acid Sites and Limiting Reagent Other three reactions were performed as described in example 2 by changing only the molar ratio between active acid sites and limiting reagent namely: 0.003, 0.007 and 0.014. The catalyst was subjected to a micronization process to a particle size ranging from 40 μm to 100 μm as measured with DLS (Dynamic light scattering) or a granulometer. The results are in the following Table 6.

TABLE 6

| catalyst (gr) | MDB (gr) | AP (gr) | Mol H+/mol reag limit | X MDB (%) | X AP (%) | Y MDP1P (%) | Y ACP (%) | S MDP1P (%) | Y By-products (%) |
|---|---|---|---|---|---|---|---|---|---|
| 0.0494 | 2.1293 | 2.2866 | 0.003 | 18 | 37 | 15 | 54 | 83 | 3 |
| 0.0990 | 2.1311 | 2.2873 | 0.007 | 49 | 80 | 40 | 99 | 81 | 9 |
| 0.2121 | 2.1310 | 2.2772 | 0.014 | 57 | 95 | 46 | 100 | 81 | 16 |

Reaction conditions: MDB:AP=1:1; temperature 80° C.; reaction time 1 h

The increase of the catalyst loading favoured the conversion of our reagents, with only a slight decrease in the product selectivity.

Example 17

Zn Exchanged AQUIVION® D79 Supported Over Silica

A reaction was performed as described in example 9 by exchanging supported AQUIVION® D79, characterized by a particle size ranging from 40 μm to 100 μm as measured with DLS (Dynamic light scattering) or a granulometer, with Zn, specifically 100% exchanged with $Zn^{2+}$.

The results are in the following Table 7.

TABLE 7

| Catalyst (gr) | MDB (gr) | AP (gr) | Exchange | X MDB (%) | X AP (%) | Y MDP1P (%) | Y ACP (%) | S MDP1P (%) | Y By-products (%) |
|---|---|---|---|---|---|---|---|---|---|
| 0.3002 | 2.1308 | 2.2910 | 100% $Zn^{2+}$ | 5 | 9 | 4 | 17 | 80 | 1 |

Conditions: MDB:AP=1:1; temperature 120° C.; reaction time 1 h.

It was evident that the exchange with a percentage of 100% of Zn had an unfavourable effect on the reaction.

Therefore the inventors found out that only with a catalyst having a partial exchange was possible acylating MDB as shown in the below example 18. The partial exchange of the catalyst according to the invention was a percentage of hydrogen atom from 5 to 80% exchanged with a metal ion selected from Fe, Zn and Ga, preferably the exchange percentage was from 10 to 50%, more preferably it was about 30%.

Example 18

Fe Exchanged AQUIVION® PW87-S

Other reactions were performed as described in example 2 at 80° C. or 120° C. by the exchanging AQUIVION® PW87-S with Fe: 50% exchanged with $Fe^{3+}$ and 100% exchanged with $Fe^{3+}$. The final catalyst was characterized by a particle size ranging from 40 μm to 100 μm as measured with DLS (Dynamic light scattering) or a granulometer. After a first cycle of reaction the catalyst was recovered, washed with 2-propanone and re-cycled.

The results are reported in the following Table 8.

TABLE 8

| CYCLE | Temperature (° C.) | Catalyst (gr) | MDB (gr) | AP (gr) | Exchange | X MDB (%) |
|---|---|---|---|---|---|---|
| I | 80 | 0.1007 | 2.1296 | 2.2809 | 50% $Fe^{3+}$ | 7 |
| II | 80 | 0.0621 | 1.3174 | 1.4058 | 50% $Fe^{3+}$ | <1 |
| I | 120 | 0.1010 | 2.1287 | 2.2795 | 100% $Fe^{3+}$ | 5 |
| II | 120 | 0.0617 | 1.3054 | 1.4037 | 100% $Fe^{3+}$ | <1 |

| CYCLE | X AP (%) | Y MDP1P (%) | Y ACP (%) | S MDP1P (%) | Y By-products (%) |
|---|---|---|---|---|---|
| I | 24 | 7 | 36 | 96 | <1 |
| II | 9 | <1 | 20 | 0 | <1 |
| I | 11 | 1 | 11 | 16 | 3 |
| II | <1 | <1 | 5 | 0 | <1 |

Conditions: MDB:AP = 1:1; reaction time 1 h.

When the AQUIVION® is partially exchanged with an ion as Fe or Zn the conversion of MDB strongly decreases but the selectivity increases Example 19

Effect of the Catalyst Shape

Other reactions were performed as described in example 9 at 120° C. changing only the catalyst form: powder (AQUIVION® PW98) and pellets (8-14 mesh, AQUIVION® P98), the sole former was subjected to a micronization process to a particle size ranging from 40 μm to 100 μm as measured with DLS (Dynamic light scattering) or a granulometer. The results are reported in the following Table 9.

TABLE 9

| catalyst (gr) | MDB (gr) | AP (gr) | Form | X MDB (%) | X AP (%) | Y MDP1P (%) | Y ACP (%) | S MDP1P (%) | Y By-products (%) |
|---|---|---|---|---|---|---|---|---|---|
| 0.1114 | 2.1273 | 2.2855 | Powder | 63 | 94 | 42 | 100 | 67 | 22 |
| 0.1154 | 2.1282 | 2.2883 | Pellets | 18 | 26 | 10 | 31 | 56 | 8 |

Reaction conditions: molar ratio between active acid sites and limiting reagent equal to 0.007; MDB:AP = 1:1; temperature 120° C.; reaction time 1 h.

It was surprisingly noted that the catalyst having a particle size according to the invention showed better results in terms of yield, conversion and selectivity with respect to the same catalyst when used in pellets of 8-14 mesh.

Example 20

Recycle Test with AQUIVION® PW79, Regeneration with Nitric Acid 2.1303 grams of MDB and 2.2947 grams of propionic anhydride were loaded inside a 25 mL two-necked round bottom flask and stirred to get a homogeneous solution. After that 0.0903 grams of catalyst (AQUIVION® PW79), corresponding to a mol ratio between active acid sites and MDB equal to 0.007), previously subjected to a micronization process to a particle size ranging from 40 μm to 100 μm as measured with DLS (Dynamic light scattering) or a granulometer, was inserted inside the liquid mixture and the flask was equipped with two condensers. The reaction mixture was then inserted in a pre-heated oil bath at 120° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with an HP-5 (Agilent) capillary column (the temperature ramp used consisted of 6 minutes at 35° C. followed by heating with a speed of 10.00° C./min up to 280° C.), and a flame ionization detector (FID).

After the first run, the catalyst was regenerated as in Example 12 with 5 mL of solution of $HNO_3$ 20% w/w at 100° C. for 1 h, recovered, washed, dried and finally tested in the same conditions as reported above. The results were reported in the following table 10.

TABLE 10

| Cycle | X MDB (%) | X AP (%) | Y MDP1P (%) | Y ACP (%) | S MDP1P (%) | Y By-products (%) |
|---|---|---|---|---|---|---|
| | 65 | 96 | 45 | 100 | 70 | 19 |
| 1 | 63 | 100 | 42 | 100 | 66 | 20 |

Reaction conditions: molar ratio between active acid sites and MDB equal to 0.007; MDB:AP = 1:1; reaction temperature 120° C.; reaction time 1 h.

The catalyst was recovered and recycled several times by using nitric acid with evident advantages in terms of process efficiency.

Example 21

Recycle Test with AQUIVION® PW79, Regeneration with Hydrochloric Acid 2.1288 grams of MDB and 2.2972 grams of propionic anhydride were loaded inside a 25 mL two-necked round bottom flask and stirred to get a homogeneous solution. After that 0.0902 grams of catalyst AQUIVION® PW79, corresponding to a mol ratio between active acid sites and MDB equal to 0.007) previously subjected to a micronization process to a particle size ranging from 40 μm to 100 μm as measured with DLS (Dynamic light scattering) or a granulometer, was inserted inside the liquid mixture and the flask was equipped with two condensers. The reaction mixture was then inserted in a pre-heated oil bath at 120° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with an HP-5 (Agilent) capillary column (the temperature ramp used consisted of 6 minutes at 35° C. followed by heating with a speed of 10.00° C./min up to 280° C.), and a flame ionization detector (FID).

After the first run, the catalyst was regenerated as in Example 12 with 5 mL of solution of HCl 20% w/w at 100° C. for 1 h, recovered, washed, dried and finally tested in the same conditions as reported above. The results are reported in the following table 11.

TABLE 11

| Cycle | X MDB (%) | X AP (%) | Y MDP1P (%) | Y ACP (%) | S MDP1P (%) | Y By-products (%) |
|---|---|---|---|---|---|---|
| | 65 | 97 | 45 | 100 | 70 | 19 |
| 1 | 63 | 95 | 43 | 100 | 68 | 20 |

Reaction conditions: molar ratio between active acid sites and MDB equal to 0.007; MDB:AP = 1:1; reaction temperature 120° C.; reaction time 1 h.
The catalyst was recovered and recycled by using nitric acid with evident advantages in terms of process efficiency.

Example 22

Acylation of MDB with AMBERLYSTR 39 Catalyst as Available on the Market Having Particle Size of 200-300 μm 2.1284 grams of MDB and 2.2822 grams of propionic anhydride were loaded inside a 25 mL two-necked round bottom flask and stirred to get a homogeneous solution. After that 0.1003 grams of catalyst AMBERLYST® 39, corresponding to a mol ratio between active acid sites and MDB equal to 0.029) as available on the market having a particle size ranging from 200 μm to 300 μm as measured with DLS (Dynamic light scattering) or a granulometer, was inserted inside the liquid mixture and the flask was equipped with two condensers. The reaction mixture was then inserted in a pre-heated oil bath at 120° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with an HP-5 (Agilent) capillary column (the temperature ramp used consisted of 6 minutes at 35° C. followed by heating with a speed of 10.00° C./min up to 280° C.), and a flame ionization detector (FID). The results were the following: MDB conversion of 42%, propionic anhydride conversion of 65%, 3,4-methylenedioxypropiophenone yield of 29% and selectivity of 69%

Example 23

Figure 2:
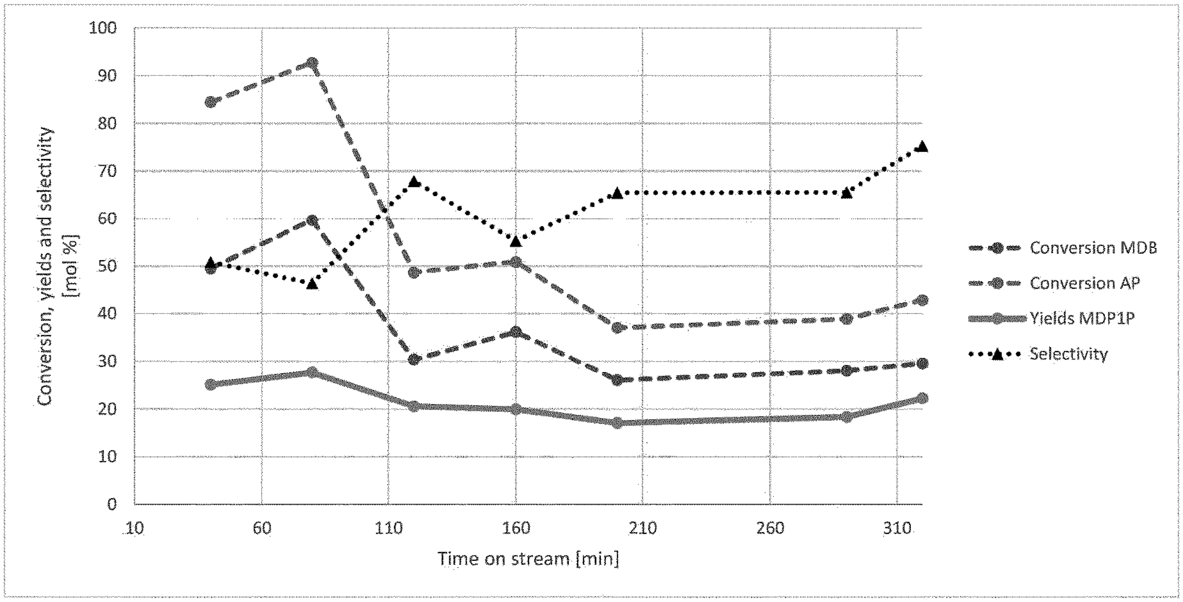
FIG. 2 represents the results of example 23.

Acylation of MDB with Micronized AMBERlYST® 30 Catalyst and Recycle Test, Regeneration with Nitric Acid 2.1284 grams of MDB and 2.2822 grams of propionic anhydride were loaded inside a 25 mL two-necked round bottom flask and stirred to get a homogeneous solution. After that 0.1003 grams of catalyst AMBERLYST® 39, corresponding to a mol ratio between active acid sites and MDB equal to 0.029) previously subjected to a micronization process to a particle size ranging from 40 μm to 100 μm as measured with DLS (Dynamic light scattering) or a granulometer, was inserted inside the liquid mixture and the flask was equipped with two condensers. The reaction mixture was then inserted in a pre-heated oil bath at 120° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with an HP-5 (Agilent) capillary column (the temperature ramp used consisted of 6 minutes at 35° C. followed by heating with a speed of 10.00° C./min up to 280° C.), and a flame ionization detector (FID). After the first run, the catalyst was regenerated as in Example 12 with 5 mL of solution of $HNO_3$ 20% w/w at 100° C. for 1 h, recovered, washed, dried and finally tested in the same conditions as reported above. The results are reported in the following table 12 and represented in FIG. 2.

TABLE 12

| Cycle | X MDB (%) | X AP (%) | Y MDP1P (%) | Y ACP (%) | S MDP1P (%) | Y By-products (%) |
|---|---|---|---|---|---|---|
| | 54 | 87 | 40 | 100 | 74 | 14 |
| 1 | 60 | 92 | 45 | 100 | 75 | 15 |

Reaction conditions: molar ratio between active acid sites and MDB equal to 0.029; MDB:AP = 1:1; reaction temperature 120° C.; reaction time 1 h.
The catalyst was recovered and recycled several times by using hydrochloric acid with evident advantages in terms of process efficiency.
The use of the catalyst in the preferred range of size particle allowed to obtain higher conversion and better selectivity.

Example 24

Acylation of MDB with NAFION™ NR50 Catalyst as Available on the Market Having Particle Size of 400-600 μm 2.1274 grams of MDB and 2.2815 grams of propionic anhydride were loaded inside a 25 mL two-necked round bottom flask and stirred to get a homogeneous solution. After that 0.1419 grams of catalyst NAFION™ NR50, corresponding to a mol ratio between active acid sites and MDB equal to 0.007), as available on the market having a particle size ranging from 400 μm to 600 μm as measured with a granulometer, was inserted inside the liquid mixture and the flask was equipped with two condensers. The reaction mixture was then inserted in a pre-heated oil bath at 120° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with an HP-5 (Agilent) capillary column (the temperature ramp used consisted of 6 minutes at 35° C. followed by heating with a speed of 10.00° C./min up to 280° C.), and a flame ionization detector (FID). The results were the following: MDB conversion of 20%, propionic anhydride conversion of 29%, 3,4-methylenedioxypropiophenone yield of 11% and selectivity of 56%

Example 25

Acylation of MDB with NAFION™ NR50 Catalyst Having Particle Size According to the Invention As a general procedure, 2.1274 grams of MDB and 2.2815 grams of propionic anhydride were loaded inside a 25 mL two-necked round bottom flask and stirred to get a homogeneous solution. After that 0.1419 grams of catalyst NAFION™ NR50, corresponding to a mol ratio between active acid sites and MDB equal to 0.007), previously subjected to a micronization process to a particle size ranging from 150 μm to 300 μm as measured with a granulometer, was inserted inside the liquid mixture and the flask was equipped with two condensers. The reaction mixture was then inserted in a pre-heated oil bath at 120° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with an HP-5 (Agilent) capillary column (the temperature ramp used consisted of 6 minutes at 35° C. followed by heating with a speed of 10.00° C./min up to 280° C.), and a flame ionization detector (FID). After the first run, the catalyst was regenerated as in Example 12 with 5 mL of solution of $HNO_3$ 20% w/w at 100° C. for 1 h, recovered, washed, dried and finally tested in the same conditions as reported above. The results are reported in the following table 13.

TABLE 13

| Cycle | X MDB (%) | X AP (%) | Y MDP1P (%) | Y ACP (%) | S MDP1P (%) | Y By-products (%) |
|---|---|---|---|---|---|---|
| | 62 | 92 | 39 | 99 | 63 | 21 |
| 1 | 62 | 93 | 40 | 97 | 64 | 21 |

Reaction conditions: molar ratio between active acid sites and MDB equal to 0.007; MDB:AP = 1:1; reaction temperature 120° C.; reaction time 1 h.

The inventors noted that the catalyst according to the invention allowed better conversions, yield and selectivity with respect to the same catalyst not micronized in the inventive range.

Example 26

Catalytic Test Under Continuous Flow Conditions

The catalytic test was performed in a fixed-bed lab-scale reactor, operating under continuous-flow at atmospheric pressure. Firstly 0.1799 grams (0.4 ml) of catalyst (AQUIVION® PW79), previously subjected to a micronization process to a particle size ranging from 40 μm to 100 μm as measured with DLS (Dynamic light scattering) or a granulometer, mixed with carborundum (total volume 0.6 mL) was inserted inside the reactor consisting of a stainless-steel tube ¼" (with quartz wool at the beginning and the end of the reactor). The reactor was wrapped with a heating band and finally covered with insulating ceramic fabric bandages. When the system reached the temperature of 150° C. the reagent mixture (composed by 26.007 grams of MDB and 28.631 grams of propionic anhydride) (1/1 mol/mol) was fed through a high precision HPLC pump at 0.05 mL/min. The reaction time started from the exit of the first drop of mixture from the outlet line of the system. Samples were taken every 10 minutes. From each sampling 50 μL of the mixture was diluted in 10 mL of acetone HPLC grade, 20 μL of octane was used as internal standard for the gas-chromatograph quantifications. The analysis of the products at the end of the reaction was carried out by a GC equipped with an HP-5 (Agilent) capillary column (the temperature ramp used consisted of 6 minutes at 35° C. followed by heating with a speed of 10.00° C./min up to 280° C.), and a flame ionization detector (FID). The results corresponding to relevant time points are reported in the following Table 14.

TABLE 14

| Time (min) | X MDB (%) | Y MDP1P (%) |
|---|---|---|
| 40 | 50 | 25 |
| 80 | 60 | 27 |
| 120 | 30 | 20 |
| 160 | 36 | 20 |
| 200 | 26 | 17 |
| 290 | 28 | 18 |
| 320 | 29 | 22 |

Reaction conditions:
MDB:AP = 1:1;
reaction temperature 150° C.;
flow 0.05 mL/min.

Example 27

Regeneration of PW87 Catalyst with $H_2O_2$ 2.1417 grams of MDB and 2.2994 grams of propionic anhydride were loaded inside a 25 mL two-necked round bottom flask and stirred to get a homogenous solution. After that 0.1004 grams of catalyst (AQUIVION® PW87-S), corresponding to a mol ratio between active acid sites and MDB equal to 0.007), previously subjected to a micronization process to a particle size ranging from 40 μm to 100 μm as measured with DLS (Dynamic light scattering) or a granulometer was inserted inside the liquid mixture and the flask was equipped with two condensers. The reaction mixture was then inserted in a pre-heated oil bath at 80° C.

and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with a HP-5 (Agilent) capillary column (the temperature ramp used consisted of 6 minutes at 35° C. followed by heating with a speed of 10° C./min up to 280° C.), and a flame ionization detector (FID). After that, the catalyst was regenerated as described in Example 9 using 5 mL of solution of $H_2O_2$ 30% w/w at 100° C. for 20 min instead of mineral acid, recovered, washed and dried as previously reported and tested in the same condition for the acylation reaction. The results are reported in the following Table 15.

TABLE 15

| Cycle | X MDB (%) | X AP (%) | Y MDP1P (%) | Y ACP (%) | S MDP1P (%) | Y By-products |
|---|---|---|---|---|---|---|
| | 50 | 77 | 41 | 100 | 82 | 9 |
| 1 | 51 | 83 | 44 | 100 | 86 | 15 |

reaction conditions: molar ratio between active sites and MDB equal to 0.007; MDB:AP = 1:1, reaction temperature 80° C.; reaction time 1 h.
The catalytic activity was recovered with evident advantages in terms of process efficiency.

Example 28

General Procedure for the Preparation of a Supported Catalyst with AQUIVION® (D72 or D79, or D82, or D98)

A mixture of Si (MeO) 4, distilled water, and 0.04M HCl with a weight ratio of 68:11:1 respectively was stirred for 45 min to give a clear solution. An AQUIVION® dispersion (D72 or D79, or D82, or D98) (which may contain for instance 25% w/w of resin in water or a mixture of water and alcohols), was diluted in water or water and alcohols. To the resin containing solution, was added a 0.4M NaOH aqueous solution, while stirring. The silicon containing solution prepared as described above was rapidly added to the stirred resin/NaOH solution to form a solid gel after few seconds after mixing. The solid was dried overnight in an oven at 95° C. After pulverization, the obtained powder was reacidified by stirring with a suitable amount of 3.5M HCl aqueous solution, and then washed with deionized water. This process was repeated 4 times. The catalyst was then treated with 25% w/w $HNO_3$ overnight at 75° C., washed with deionized water and dried at 100° C. for 12 h.

Example 29

Synthesis of Catalysts Containing 13 wt % AQUIVION® Supported into Silica

A mixture of 12.6706 g of Si (MeO) 4, 2.0497 g of distilled water, and 0.1863 g of 0.04M HCl was stirred for 45 min to give a clear solution. A mixture of 2.9712 g of AQUIVION® D72 (or D79, or D82, or D98) resin solution (which contains 25% w/w of resin), 8 g of distilled water, and 9.96 g of 1-propanol was prepared. To the resin containing solution, was added 10.3 mL of a 0.4M NaOH aqueous solution, while stirring. The silicon containing solution prepared as described above was rapidly added to the stirred resin/NaOH solution to form a solid gel after few seconds after mixing. The solid was dried overnight in an oven at 95° C. After grinding, the obtained powder having particle size ranging from 40 μm to 100 μm was reacidified by stirring with 50 mL of 3.5M HCl aqueous solution, and then washed with deionized water. This process was repeated 4 times. The catalyst was then treated with 25% w/w $HNO_3$ overnight at 75° C., washed with deionized water and dried at 100° C. for 12 h.

Example 30

Synthesis of Catalysts Containing 13 wt % NAFION™ Supported into Silica

A mixture of 7.6003 g of Si (MeO) 4, 1.2306 g of distilled water, and 0.1112 g of 0.04M HCl was stirred for 45 min to give a clear solution. A mixture of 2.2284 g of NAFION™ resin solution (which contains 20% w/w of resin), 3.34 g of distilled water, and 4.16 g of 1-propanol was prepared. To the resin containing solution, was added 5.52 mL of a 0.4M NaOH aqueous solution, while stirring. The silicon containing solution prepared as described above was rapidly added to the stirred resin/NaOH solution to form a solid gel after few seconds after mixing. The solid was dried overnight in an oven at 95° C. After grinding, the obtained powder having particle size ranging from 40 μm to 100 μm was reacidified by stirring with 50 mL of 3.5M HCl aqueous solution, and then washed with deionized water. This process was repeated 4 times. The catalyst was then treated with 25% w/w $HNO_3$ overnight at 75° C., washed with deionized water and dried at 100° C. for 12 h.

Example 31

Process of the Invention with Catalyst AQUIVION® D72 Supported into Silica 2.1458 grams of MDB and 2.3081 grams of propionic anhydride were loaded inside a 25 mL two-necked round bottom flask and stirred to get a homogenous solution. After that 0.6726 grams of catalyst AQUIVION® D72 13% w/w over silica, corresponding to a mol ratio between active acid sites and MDB equal to 0.007) produced with a particle size in range from 40 μm to 100 μm was inserted inside the liquid mixture and the flask was equipped with two condensers. The reaction mixture was then inserted in a pre-heated oil bath at 80° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with a HP-5 (Agilent) capillary column (the temperature ramp used consisted of 6 minutes at 35° C. followed by heating with a speed of 10° C./min up to 280° C.), and a flame ionization detector (FID). The results were the following: MDB conversion of 59%, propionic anhydride conversion of 90%, 3,4-methylenedioxypropiophenone yield of 50% and selectivity of 85%, by-products yield of 9%.

Example 32

Acylation of the Invention with Catalyst AQUIVION® D79 Supported into Silica 2.1354 grams of MDB and 2.2956 grams of propionic anhydride were loaded inside a 25 mL two-necked round bottom flask and stirred to get a homogenous solution. After that 0.7448 grams of catalyst AQUIVION® D79 13% w/w over silica, corresponding to a mol ratio between active acid sites and MDB equal to 0.007), produced with a particle size in range from 40 μm to 100 μm, was inserted inside the liquid mixture and the flask was equipped with two condensers. The reaction mixture was then inserted in a pre-heated oil bath at 80° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with a HP-5 (Agilent) capillary column (the temperature ramp used consisted of 6 minutes at 35° C. followed by heating with a speed of 10° C./min up to 280° C.), and a flame ionization detector (FID). The results were the following: MDB conversion of 50%, propionic anhydride conversion of 85%, 3,4-methylenedioxypropiophenone yield of 43% and selectivity of 86%, by-products yield of 7%.

Example 33

Acylation of the Invention with Catalyst AQUIVION® D83 Supported into Silica 2.1402 grams of MDB and 2.3039 grams of propionic anhydride were loaded inside a 25 mL two-necked round bottom flask and stirred to get a homogenous solution. After that 0.7754 grams of catalyst AQUIVION® D83 13% w/w over silica, corresponding to a mol ratio between active acid sites and MDB equal to 0.007), produced with a particle size in range from 40 μm to 100 μm, was inserted inside the liquid mixture and the flask was equipped with two condensers. The reaction mixture was then inserted in a pre-heated oil bath at 80° C. and the reaction was performed under magnetic stirring (500 rpm) for 1 hour. After the reaction, the mixture was rapidly cooled in an ice bath and the reaction mixture was recovered in 50 ml of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with a HP-5 (Agilent) capillary column (the temperature ramp used consisted of 6 minutes at 35° C. followed by heating with a speed of 10° C./min up to 280° C.), and a flame ionization detector (FID). The results were the following: MDB conversion of 51%, propionic anhydride conversion of 86%, 3,4-methylenedioxypropiophenone yield of 42% and selectivity of 83%, by-products yield of 7%.

Example 34

Process of the Invention with Catalyst AQUIVION®D98 Supported into Silica

As a general procedure, 1.0673 grams of MDB and 1.1502 grams of propionic anhydride were loaded inside a 25 mL two-necked round bottom flask and stirred to get a homogenous solution. After that 0.4589 grams of catalyst AQUIVION® D98 13% w/w over silica, corresponding to a mol ratio between active acid sites and MDB equal to 0.007), produced with a particle size in range from 40 μm to 100 μm, was inserted inside the liquid mixture and the flask was equipped with two condensers. The reaction mixture was then inserted in a pre-heated oil bath at 80° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with a HP-5 (Agilent) capillary column (the temperature ramp used consisted of 6 minutes at 35° C. followed by heating with a speed of 10° C./min up to 280° C.), and a flame ionization detector (FID). The results were the following: MDB conversion of 49%, propionic anhydride conversion of 86%, 3,4-methylenedioxypropiophenone yield of 42% and selectivity of 85%, by-products.

Example 35

Process of the Invention with Catalyst AQUIVION® D72 (5% w/w) Supported into Silica As a general procedure, 2.146 grams of MDB and 2.3044 grams of propionic anhydride were loaded inside a 25 mL two-necked round bottom flask and stirred to get a homogenous solution. After that 1.762 grams of catalyst obtained as described in Example 29 modifying the amount of resin loading AQUIVION® D72 5% w/w over silica, corresponding to a mol ratio between active acid sites and MDB equal to 0.007), produced with a particle size in range from 40 μm to 100 μm, was inserted inside the liquid mixture and the flask was equipped with two condensers. The reaction mixture was then inserted in a pre-heated oil bath at 80° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with a HP-5 (Agilent) capillary column (the temperature ramp used consisted of 6 minutes at 35° C. followed by heating with a speed of 10° C./min up to 280° C.), and a flame ionization detector (FID). The results were the following: MDB conversion of 39%, propionic anhydride conversion of 96%, 3,4-methylenedioxypropiophenone yield of 33% and selectivity of 86%, by-products yield of 3%.

Example 36

Process of the Invention with Catalyst AQUIVION® D72 (30% w/w) Supported into Silica As a general procedure, 2.152 grams of MDB and 2.3269 grams of propionic anhydride were loaded inside a 25 mL two-necked round bottom flask and stirred to get a homogenous solution. After that 0.2941 grams of catalyst obtained as described in Example 29 modifying the amount of resin loading AQUIVION® D72 30% w/w over silica, corresponding to a mol ratio between active acid sites and MDB equal to 0.007), produced with a particle size in range from 40 μm to 100 μm, was inserted inside the liquid mixture and the flask was equipped with two condensers. The reaction mixture was then inserted in a pre-heated oil bath at 80° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with a HP-5 (Agilent) capillary column (the temperature ramp used consisted of 6 minutes at 35° C. followed by heating with a speed of 10° C./min up to 280° C.), and a flame ionization detector (FID). The results were the following: MDB conversion of 47%, propionic anhydride conversion of 78%, 3,4-methylenedioxypropiophenone yield of 42% and selectivity of 88%, by-products yield of 8%.

Example 37

Process of the Invention with Catalyst NAFION™ (13% w/w) Supported into Silica As a general procedure, 1.4281 grams of MDB and 1.5415 grams of propionic anhydride were loaded inside a 25 mL two-necked round bottom flask and stirred to get a homogenous solution. After that 0.630 grams of catalyst obtained as described in Example 29 NAFION™13% w/w over silica, corresponding to a mol ratio between active acid sites and MDB equal to 0.007), produced with a particle size in range from 40 μm to 100 μm, was inserted inside the liquid mixture and the flask was equipped with two condensers. The reaction mixture was then inserted in a preheated oil bath at 80° C. and the reaction was performed under magnetic stirring (500 rpm) for 1 hour. After the reaction, the mixture was rapidly cooled in an ice bath and the reaction mixture was recovered in 50 mL of acetone HPLC grade. 0.8 mL of the mixture was diluted in 10 mL of acetone HPLC grade, 20 μL of octane was used as internal standard for the gas-chromatograph quantifications. The analysis of the products at the end of the reaction was carried out by a GC equipped with a HP-5 (Agilent) capillary column (the temperature ramp used consisted of 6 minutes at 35° C. followed by heating with a speed of 10° C./min up to 280° C.), and a flame ionization detector (FID). The results were the following: MDB conversion of 49%, propionic anhydride conversion of 85%, 3,4-methylenedioxypropiophenone yield of 41% and selectivity of 85%, by-products yield of 6%.

The invention claimed is:

1. A process for the preparation of 1-(1,3-benzodioxol-5-yl)-1-propanone comprising the step of reacting 3,4-methylendioxybenzene with propionic anhydride in the presence of a bulk or supported catalyst, being said catalyst selected from the group of sulphonated cross-linked polystyrene-divinylbenzene resins, sulphonated cross-linked polystyrene-divinylbenzene resins partially exchanged with iron, zinc or gallium, perfluorinated sulphonic resins, and perfluorinated sulphonic resins partially exchanged with iron, zinc or gallium, wherein said catalyst has an average particle size from 1 μm to 300 μm as measured with DLS (Dynamic light scattering) or a granulometer.

2. The process according to claim 1, wherein the bulk or supported catalyst is a sulphonated cross-linked polystyrene-divinyl benzene resin used as bulk or supported on silica, said sulphonated cross-linked polystyrene-divinyl benzene resin being characterized by an acid loading expressed as mmol of group —$SO_3H$ per g of material in the range from 2 to 6.

3. The process according to claim 1, wherein the bulk or supported catalyst is a perfluorinated sulphonic acid resins used as bulk or supported on silica, said perfluorinated sulphonic acid resin being characterized by an acid loading expressed as mmol of group —$SO_3H$ per g of material in the range from 0.2 to 2.

4. The process according to claim 1, wherein the bulk or supported catalyst is a sulphonated cross-linked polystyrene-divinyl benzene resin or a perfluorinated sulphonic acid resin partially exchanged with iron or zinc or gallium, wherein the partial exchange is a percentage of hydrogen atom from 5 to 80% exchanged with a metal ion selected from Fe, Zn and Ga.

5. The process according to claim 1, wherein the catalyst is supported over suitable inorganic oxides.

6. The process according to claim 5, wherein the catalysts are supported on the inorganic oxides in a percentage by weight (%) from 1 to 60 by weight with respect to the total weight of the supported catalyst.

7. The process according to claim 1, wherein the step of reacting 3,4-methylendioxybenzene with propionic anhydride is carried out in the range of temperature from 50 to 200° C.

8. The process according to claim 7, wherein the reaction time is from 5 to 240 min.

9. The process according to claim 1, wherein the step of reacting 3,4-methylendioxybenzene with propionic anhydride is carried out in the range of temperature from 50 to 150° C.

10. The process according to claim 9, wherein the reaction time is from 5 to 240 min.

11. The process according to claim 1, wherein the amount of catalyst expressed as ratio between mol of H+ or of active sites per mol of limiting reagent is from 0.0001 to 1.

12. The process according to claim 1, wherein the amount of catalyst expressed as ratio between mol of H+ or of active sites per mol of limiting reagent is from 0.002 to 1.

13. The process according to claim 1, wherein the step of reacting 3,4-methylendioxybenzene with propionic anhydride is carried out with a molar ratio between 3,4-methylendioxybenzene and propionic anhydride in the range from 2 to 1 to 1 to 2.

14. The process according to claim 1, wherein the catalyst is recovered, regenerated and recycled.

15. The process according to claim 14, wherein the catalyst is recovered by filtration from the reaction medium and suspended in a diluted acid aqueous solution of nitric acid.

16. The process according to claim 14, wherein the catalyst is recovered by filtration from the reaction medium and suspended in a diluted acid aqueous solution of hydrochloric acid.

17. The process according to claim 14, wherein the recovery of the catalyst is carried out at a temperature in the range from room temperature to reflux for a time in the range from few minutes to 4 hours.

18. The process according to claim 14, wherein the recovery, the regeneration and the recycle of the catalyst is carried out with the use of $H_2O_2$.

19. The process according to claim 1, wherein said catalyst has an average particle size from 40 μm to 100 μm.

20. The process according to claim 1, wherein the process is a continuous process.

21. The process according to claim 1, wherein said catalyst has an average particle size from 1 μm to 180 μm as measured with DLS (Dynamic light scattering) or a granulometer.

22. The process according to claim 21, wherein said catalyst has an average particle size from 1 μm to 100 μm as measured with DLS (Dynamic light scattering) or a granulometer.

23. The process according to claim 21, wherein the acid loading, expressed as mmol of group —$SO_3H$ per g of material is in the range from 2.5 to 5.5.

24. The process according to claim 23, wherein the acid loading, expressed as mmol of group —$SO_3H$ per g of material is 5.

25. The process according to claim 3, wherein the acid loading, expressed as mmol of group —$SO_3H$ per g of material is in the range from 0.7 to 1.6.

26. The process according to claim 25, wherein the acid loading, expressed as mmol of group —$SO_3H$ per g of material is 1.2.

27. The process according to claim 4, wherein the exchange percentage is from 10 to 50%.

28. The process according to claim 27, wherein the exchange percentage is 30%.

29. The process according to claim 5, wherein the inorganic oxides are selected from zirconia, alumina, titania and silica.

30. The process according to claim 29, wherein the inorganic oxides are selected from silica.

31. The process according to claim 6, wherein the catalysts are supported on the inorganic oxides in a percentage by weight (%) from 5 to 30 with respect to the total weight of the supported catalyst.

32. The process according to claim 31, wherein the catalysts are supported on the inorganic oxides in a percentage by weight (%) from 10 to 15 with respect to the total weight of the supported catalyst.

33. The process according to claim 7, wherein the temperature is in the range from 60 to 150° C.

34. The process according to claim 33, wherein the temperature is 80° C.

35. The process according to claim 8, wherein the reaction time is from 5 to 120 min.

36. The process according to claim 35, wherein the reaction time is 60 min.

37. The process according to claim 9, wherein the temperature is in the range from 60 to 130° C.

38. The process according to claim 37, wherein the temperature is 80° C. or 130° C.

39. The process according to claim 10, wherein the reaction time is from 5 to 120 min.

40. The process according to claim 39, wherein the reaction time is 60 min.

41. The process according to claim 11, wherein the amount of catalyst is from 0.001 to 0.04.

42. The process according to claim 41, wherein the amount of catalyst is 0.007.

43. The process according to claim 12, wherein the amount of catalyst is from 0.01 to 0.08.

44. The process according to claim 43, wherein the amount of catalyst is 0.03.

45. The process according to claim 13, wherein the molar ratio is 1:1 stoichiometric ratio.

46. The process according to claim 15, wherein the concentration of the diluted acid aqueous solution of nitric acid is in the range from 2% wt to 60% wt.

47. The process according to claim 46, wherein the concentration of the diluted acid aqueous solution of nitric acid is in the range from 10% wt to 40% wt.

48. The process according to claim 47, wherein the concentration of the diluted acid aqueous solution of nitric acid is 20% wt.

49. The process according to claim 16, wherein the concentration of the diluted acid aqueous solution of hydrochloric acid is in the range from 2% wt to 30% wt.

50. The process according to claim 49, wherein the concentration of the diluted acid aqueous solution of hydrochloric acid is 20% wt.

51. The process according to claim 17, wherein the time is 1 hour.

* * * * *